(12) United States Patent
Bernstein et al.

(10) Patent No.: US 8,679,122 B2
(45) Date of Patent: Mar. 25, 2014

(54) SYSTEM FOR TENSIONING A SURGICAL WIRE

(75) Inventors: Oren Simon Bernstein, Portland, OR (US); Howard K. Song, Portland, OR (US); Alexander Robson Legg, Lebanon, OR (US); Joel Gillard, Portland, OR (US)

(73) Assignee: Acute Innovations LLC, Hillsboro, OR (US)

( * ) Notice: Subject to any disclaimer, the term of this patent is extended or adjusted under 35 U.S.C. 154(b) by 617 days.

(21) Appl. No.: 12/903,024

(22) Filed: Oct. 12, 2010

(65) Prior Publication Data

US 2011/0112537 A1 May 12, 2011

Related U.S. Application Data

(60) Provisional application No. 61/250,389, filed on Oct. 9, 2009.

(51) Int. Cl.
*A61B 17/58* (2006.01)
*A61B 17/82* (2006.01)
*A61F 2/30* (2006.01)

(52) U.S. Cl.
USPC .......................................................... 606/74

(58) Field of Classification Search
USPC .................. 606/53, 60, 74, 246, 263, 300
See application file for complete search history.

(56) References Cited

U.S. PATENT DOCUMENTS

| | | | |
|---|---|---|---|
| 2,049,361 A * | 7/1936 | Ericsson | 606/103 |
| 2,455,609 A * | 12/1948 | Scheib | 606/103 |
| 2,943,650 A * | 7/1960 | Rubin | 140/119 |
| 3,507,270 A | 4/1970 | Ferrier | |
| 3,759,302 A | 9/1973 | Attenborough | |
| 4,050,464 A | 9/1977 | Hall | |
| 4,269,180 A | 5/1981 | Dall et al. | |
| 4,587,963 A | 5/1986 | Leibinger et al. | |
| 4,649,916 A * | 3/1987 | Frimberger | 606/1 |
| 4,712,542 A | 12/1987 | Daniel et al. | |
| 4,936,843 A | 6/1990 | Sohngen | |
| 5,057,113 A | 10/1991 | Mingozzi | |
| 5,116,340 A | 5/1992 | Songer et al. | |
| 5,190,545 A | 3/1993 | Corsi et al. | |
| 5,312,410 A | 5/1994 | Miller et al. | |
| 5,395,374 A | 3/1995 | Miller et al. | |
| 5,545,168 A | 8/1996 | Burke | |
| 5,609,596 A | 3/1997 | Pepper | |
| 5,704,936 A | 1/1998 | Mazel | |

(Continued)

FOREIGN PATENT DOCUMENTS

| | | |
|---|---|---|
| GB | 2214113 A | 8/1989 |
| WO | 2004037463 | 5/2004 |
| WO | 2008073947 | 6/2008 |

OTHER PUBLICATIONS

"Examination Report Under Section 18(3)" in connection with related U.K. Application No. GB1017102.3, dated May 9, 2013, 2 pages.

(Continued)

*Primary Examiner* — Anu Ramana
(74) *Attorney, Agent, or Firm* — Kolisch Hartwell, P.C.

(57) ABSTRACT

System, including methods, apparatus, and kits, for tensioning a surgical wire with a tensioning device and/or fixing bone with a surgical wire tensioned with a tensioning device.

19 Claims, 5 Drawing Sheets

(56) References Cited

U.S. PATENT DOCUMENTS

| | | | |
|---|---|---|---|
| 5,713,897 A * | 2/1998 | Goble et al. | 606/53 |
| 5,741,259 A | 4/1998 | Chan | |
| 5,788,697 A | 8/1998 | Kilpela et al. | |
| 5,810,825 A | 9/1998 | Huebner | |
| 5,902,305 A | 5/1999 | Beger et al. | |
| 5,935,130 A | 8/1999 | Kilpela et al. | |
| 5,935,133 A | 8/1999 | Wagner et al. | |
| 5,941,881 A | 8/1999 | Barnes | |
| 5,971,178 A | 10/1999 | Ratcliff et al. | |
| 5,993,452 A | 11/1999 | Vandewalle | |
| 6,017,347 A | 1/2000 | Huebner et al. | |
| 6,120,505 A | 9/2000 | Huebner | |
| 6,146,386 A | 11/2000 | Blackman et al. | |
| 6,364,885 B1 | 4/2002 | Kilpela et al. | |
| 6,443,955 B1 | 9/2002 | Ahrend et al. | |
| 6,595,994 B2 | 7/2003 | Kilpela et al. | |
| 6,616,667 B1 | 9/2003 | Steiger et al. | |
| 6,679,889 B1 | 1/2004 | West, Jr. et al. | |
| 6,752,810 B1 | 6/2004 | Gao et al. | |
| 7,175,162 B1 | 2/2007 | Ratcliff | |
| 7,326,222 B2 | 2/2008 | Dreyfuss et al. | |
| 2003/0178611 A1 | 9/2003 | Anderson | |
| 2005/0107797 A1 | 5/2005 | Romeo | |
| 2005/0137608 A1 | 6/2005 | Hearn et al. | |
| 2006/0058795 A1 | 3/2006 | Boyd | |
| 2006/0276804 A1 | 12/2006 | Molz, IV et al. | |
| 2007/0260248 A1 | 11/2007 | Tipirneni | |
| 2010/0094294 A1 | 4/2010 | Gillard et al. | |

OTHER PUBLICATIONS

Acumed, LLC "Osteo-Clage—Cerclage Cable System" brochure, FOCL-03-07, Copyright 2000, Rev. Apr. 2003, 2 pages.
Acumed, LLC, "Osteo-Clage Cerclage Cable System" Surgical Technique, FOCL-05-04, Nov., 2002, 2 pages.
Photo 1, Osteo-Clage Tensioner (top view).
Photo 2, Osteo-Clage Tensioner (perspective view).
Codman & Shurtleff Inc., Sof'Wire Cable System product brochure; undated.
United Kingdom Intellectual Property Office, Patents Act 1977: Search Report under Section 17(5); U.K. Patent Application No. GB1017102.3; search report date: Dec. 10, 2010; mailing date: Dec. 13, 2010.
Rhinelander F.W., "Instruments for Use with Flexible Steel Wire in Bone Surgery." J. Bone Joint Surg. Am. 1958;40-A (2):365-374.
Stryker Orthopaedics, Dall-Miles Hip Systems Recon & Trauma Cable System, print-outs from various pages <http://www.stryker.com/jointreplacements/ . . . >, accessed on Nov. 27, 2006.
Sythes, Inc., product brochure, Synthes CMF Modular Sternal Cable System, Multiple Closure Options. Flexibility and strength in sternal closure and repair (2006); Implant Reference Guide (2004).
Sythes, Inc., product brochure, Synthes CMF Modular Sternal Cable System Technique Guide. Flexibility and strength in sternal closure and repair. 2006.

* cited by examiner

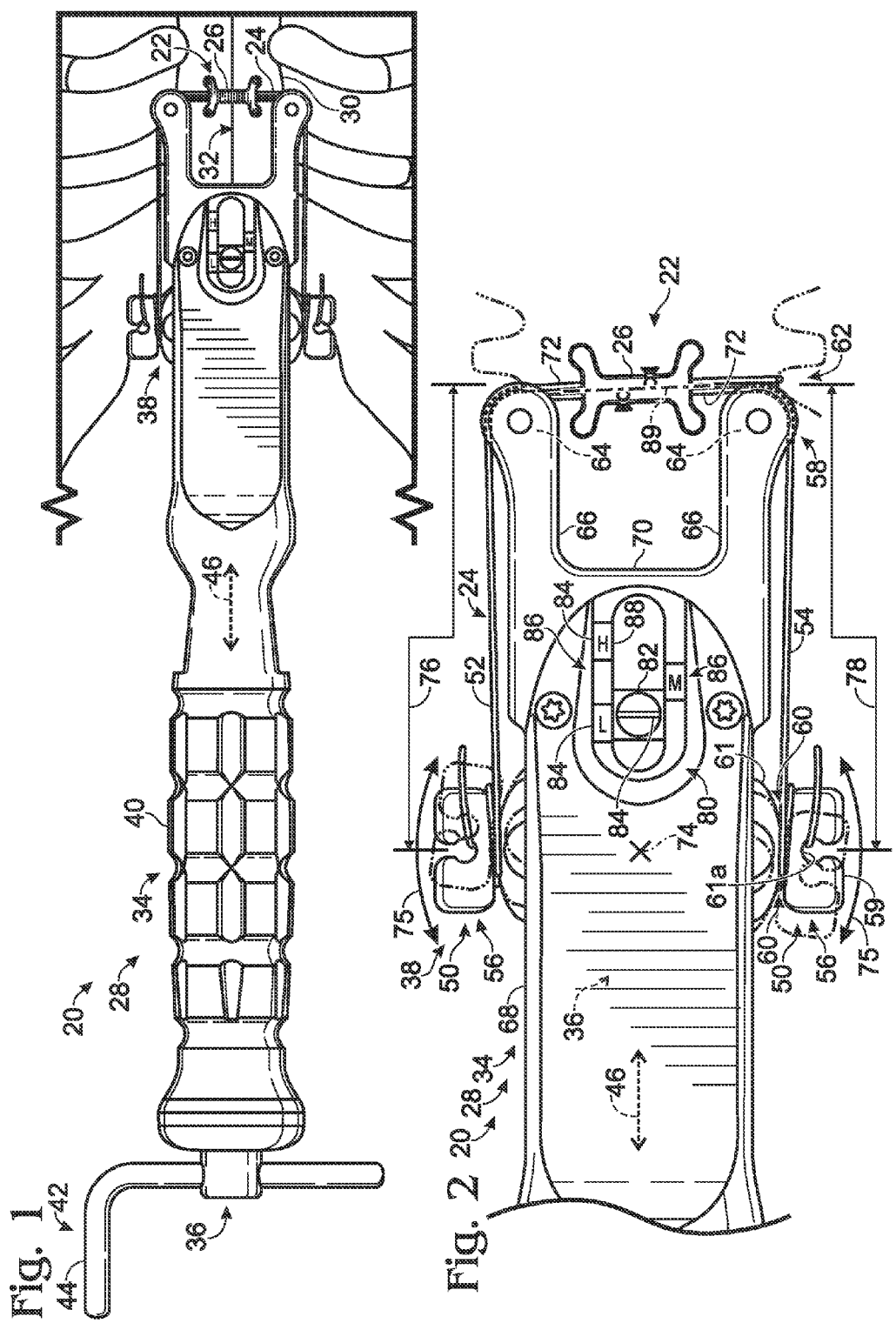

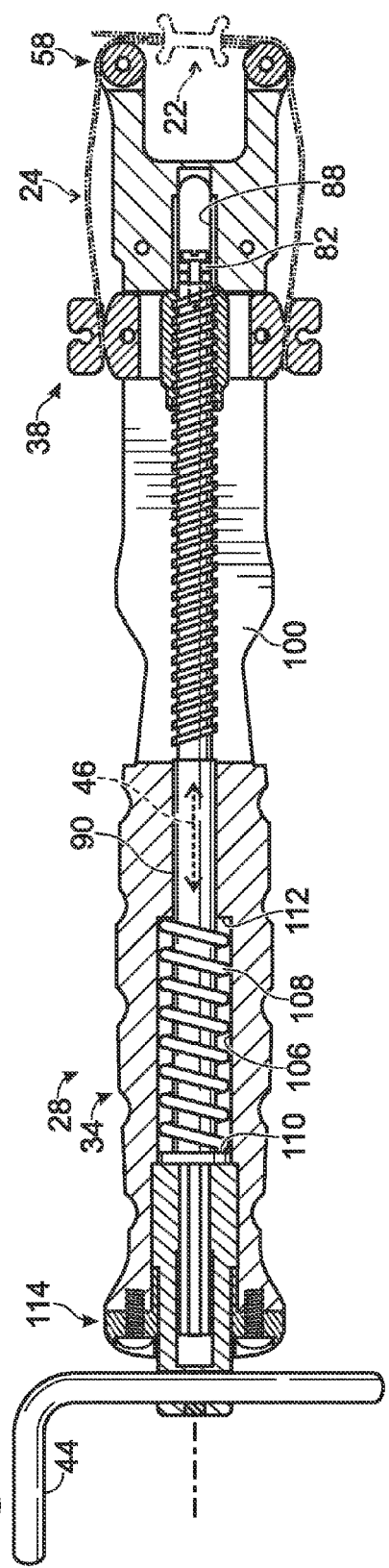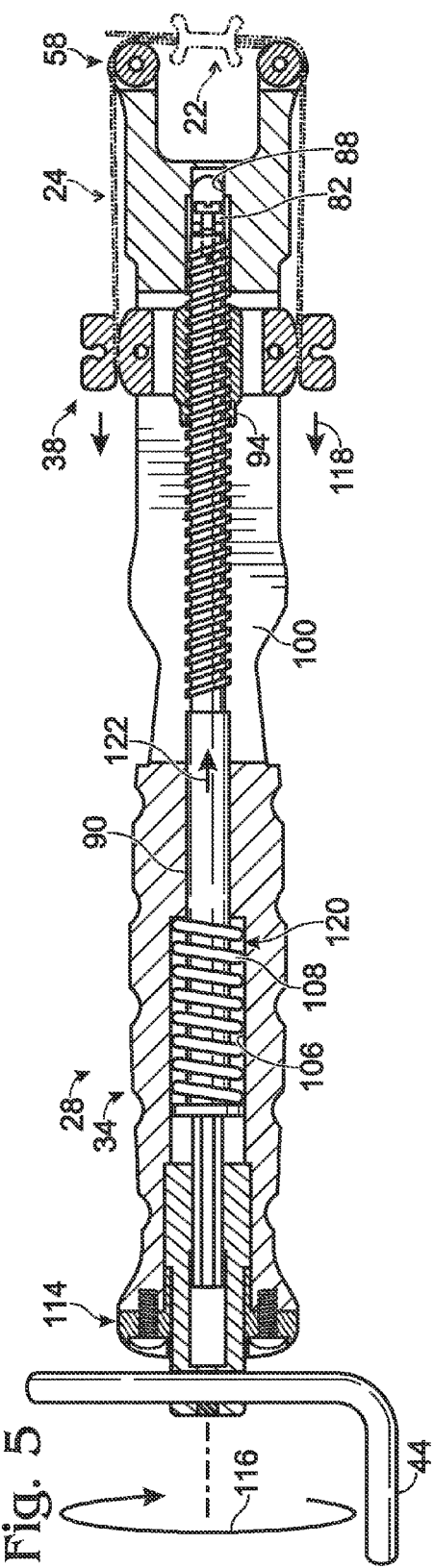

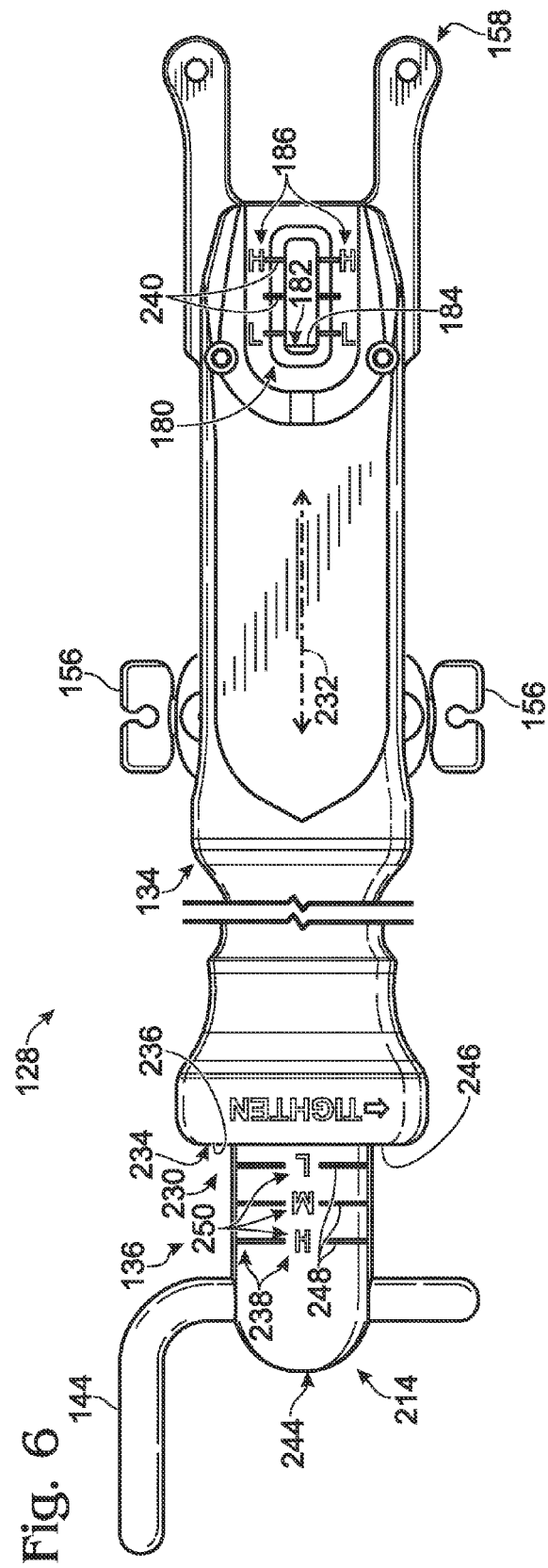

SYSTEM FOR TENSIONING A SURGICAL WIRE

CROSS-REFERENCE TO PRIORITY APPLICATION

This application is based upon and claims the benefit under 35 U.S.C. §119(e) of U.S. Provisional Patent Application Ser. No. 61/250,389, filed Oct. 9, 2009, which is incorporated herein by reference in its entirety for all purposes.

INTRODUCTION

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that are cut or broken should be repaired promptly and properly. Typically, a cut or broken bone is treated using a fixation device, which reinforces the bone and keeps it aligned during healing. Fixation devices may take a variety of forms, including casts for external fixation and implants (e.g., bone plates, nails, screws, pins, wires, etc.) for internal fixation, among others.

Some cut or broken bones are more amenable to fixation with a wire implanted in a "cerclage" configuration. In this configuration, the wire encircles bone to form a closed loop, also termed a wire suture, that compresses the bone radially.

Orthopedic cerclage may be used to fix bones of the rib cage. The rib cage, or thoracic cage, is composed of bone and cartilage that surround the chest cavity and organs therein, such as the heart and the lungs. In humans, the rib cage typically consists of 24 ribs, twelve thoracic vertebrae, the sternum (or breastbone), and the costal cartilages. The ribs articulate with the thoracic vertebrae posteriorly and, with the exception of the bottom two pairs of ribs (the floating ribs), are connected to the sternum anteriorly via the costal cartilages.

Major surgery inside the chest cavity, such as open heart surgery, generally requires that the rib cage be opened. The most common procedure for opening the rib cage is for a surgeon to place a longitudinal cut through the entire length of the sternum, from the sternal notch superiorly to the xiphoid process inferiorly. Cutting the sternum forms left and right sternal halves. The surgeon then divides or "cracks" the sternum by pulling the sternal halves apart from one another. After surgery in the chest cavity, the sternal halves are brought back into bony approximation and secured to one another.

The surgeon may secure the sternum using a cerclage procedure in which wires encircle the sternum at positions along the sternum. Each wire may be locked in a closed loop using a locking device. A commonly used locking device is structured as a sleeve or block defining a pair of side-by-side bores for receiving sections of a wire. After the wire sections are disposed in the bores and the wire is properly positioned and tensioned, the sleeve or block may be deformed, which locks the wire to the sleeve or block.

Generally, the wire is tensioned with a tensioning instrument (a "tensioner") before the wire is locked in place. The tensioner may apply an adjustable level of tension to the wire, and then maintain tension while the locking device is actuated (e.g., deformed). The tensioner may be designed to apply tension to only end of the wire or to both wire ends at the same time. Generally, tensioning both ends of the wire at the same time may be preferable, because the wire is less likely to apply pressure asymmetrically to the bone.

Wire tensioners for surgical use may be inadequate for one or more reasons. For example, the tensioner may lack a mechanism for equalizing the tension applied to the two ends of the wire, if the wire is unable to slide around bone to equalize tension on its own. As a result, the wire may dig into and damage bone on one side as the wire is tensioned. Also, the tensioner may lack any mechanism for measuring the tension applied, or such a mechanism may be present but may be difficult to use effectively during surgery. Thus, a surgeon may apply too much tension, which may damage bone or break the wire, or may apply too little tension, which may fail to fix the bone properly. Furthermore, the tensioner may lack a quick and effective mechanism for securing the ends of the wire to the tensioner in a manner that avoids wire slippage as increasing tension is applied. Due to these and other deficiencies, an improved tensioner is needed for applying tension to a surgical wire.

SUMMARY

The present disclosure provides a system, including methods, apparatus, and kits, for tensioning a surgical wire with a tensioning device and/or fixing bone with a surgical wire tensioned with a tensioning device.

BRIEF DESCRIPTION OF THE DRAWINGS

FIG. 1 is a view of selected aspects of an exemplary system for tensioning a surgical wire, with the wire assembled with an exemplary locking device to provide a cerclage assembly and being tensioned by an exemplary tensioner while extending around a cut sternum that is to be fixed by the cerclage assembly, in accordance with aspects of present disclosure.

FIG. 2 is a fragmentary view of the tensioner and cerclage assembly of FIG. 1, taken in the absence of bone.

FIG. 4 is a sectional view of the tensioner of FIG. 1, taken generally along line 4-4 of FIG. 3, in the absence of bone, with the cerclage assembly in phantom outline, and before tensioning the wire.

FIG. 5 is another sectional view of the tensioner of FIG. 1, taken as in FIG. 4 after tensioning the wire with the tensioner.

FIG. 6 is a side view of another exemplary tensioner for use with a surgical wire, in accordance with aspects of present disclosure.

DETAILED DESCRIPTION

Figure 3:
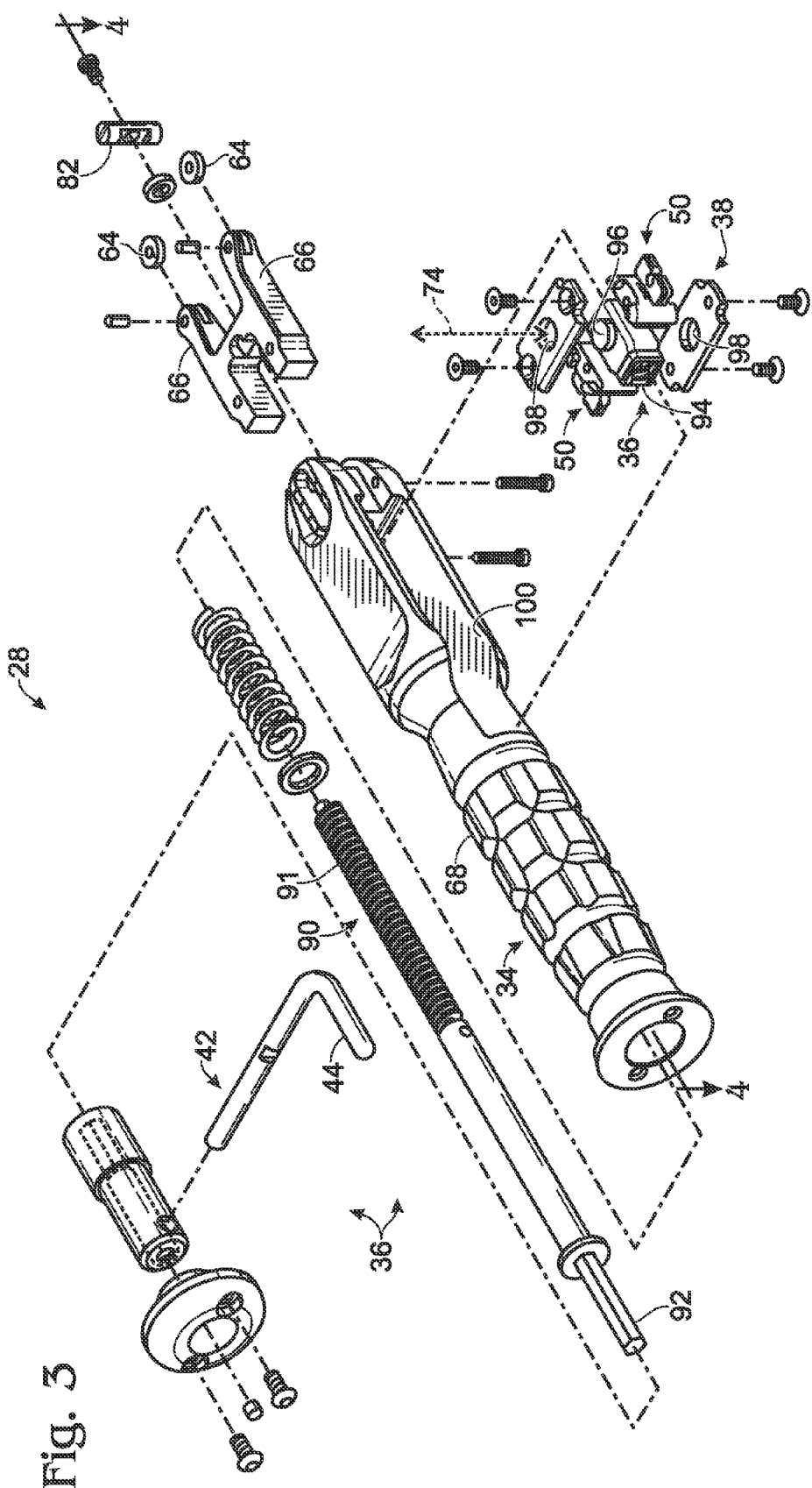
FIG. 3 is an exploded view of the tensioner of FIG. 1.

The present disclosure provides a system, including methods, apparatus, and kits, for tensioning a surgical wire with a tensioning device and/or fixing bone with a surgical wire tensioned with a tensioning device.

The system may provide a device for tensioning a surgical wire. The device may comprise a frame including a distal end portion and also may comprise a drive assembly connected to the frame and defining an axis of travel. The device further may comprise a carriage including at least one anchor site for attachment of a surgical wire or opposing anchor sites for attachment of opposing end regions of a surgical wire extending from the distal end portion of the frame. The carriage may be connected to the drive assembly such that power supplied to the drive assembly, such as by turning a portion of the drive assembly (e.g., a crank), drives the carriage away from the distal end portion of the frame, thereby providing an ability to apply tension to the wire and/or to both end regions of the wire attached to the anchor sites. In some embodiments, the carriage may be pivotable about an axis transverse (e.g., at least substantially orthogonal) to the axis of travel, to dynamically balance the tension applied to the end regions of the wire. In some embodiments, the tensioning device may include at least one tension gauge or a pair of tension gauges. In some embodiments, the drive assembly may include a drive screw that has a biased position along the axis of travel, with respect to the frame. For example, the drive screw may be spring-loaded. In any event, the drive screw may be moved from the biased position as tension on the wire is increased. This movement from the biased position may buffer the tension applied to the wire, especially with higher levels of tension, and/or may enable operation of a tension gauge. In some embodiments, the drive screw may include or be attached to a tension indicator (and/or a series of reference marks) of the tension gauge. The drive screw and tension indicator (and/or reference marks) may be held in a biased position until a sufficient force is applied to the carriage by the end regions of the wire, to force the drive screw and tension indicator (and/or reference marks) from the biased position, thereby visibly indicating a change in tension by a change in position of the tension indicator (and/or reference marks). In some embodiments, the drive screw may be attached to a portion of each of a pair of tension gauges. For example, the drive screw may be attached to a tension indicator of a first tension gauge and attached to a series of reference marks of a second tension gauge. In some embodiments, each anchor site may include a hitching bracket configured to secure an end region of a surgical wire with the end region wrapped around the hitching bracket.

A method of bone fixation may be provided. A surgical wire may be disposed around bone. Both opposing end regions of the wire may be attached to a carriage that is pivotable transverse to an axis of travel. In some examples, both end regions of the wire may be attached by wrapping the end regions around respective hitching brackets of the carriage to secure the wire to the carriage. Tension may be applied to both end regions of the wire by driving movement of the carriage away from the bone in a direction parallel to the axis of travel. The tension may be balanced dynamically between the end regions by pivotal motion of the carriage. The wire may be secured around the bone while the wire remains under tension.

The system disclosed herein has substantial advantages, which may include (1) application of more balanced or equalized tension to the ends of a surgical wire during implantation of the wire, (2) measurement of tension on a wire as the tension is being adjusted, (3) tension readings available from opposing sides and/or near both opposing ends of a tensioner, (4) application of tension to a wire more gradually and controllably, and/or (5) attachment of a wire to a tensioning device using a hitching bracket onto which the wire can be wrapped. These advantages may improve wire installation by producing less damage to bone, reducing time in the operating room, and/or securing the wire with a more reproducible and/or effective tension, among others.

Further aspects of the present disclosure are described in the following sections: (I) exemplary tensioning/fixation system, (II) wires, (III) locking devices, (IV) methods of wire tensioning and/or bone fixation, (V) kits, and (VI) examples.

I. Exemplary Tensioning/Fixation System

FIG. 1 shows an exemplary system 20 for tensioning a surgical wire and/or for fixing bone with a tensioned wire. System 20 may incorporate a cerclage assembly 22 comprising a surgical wire 24, and, optionally, a wire-locking device 26 that secures the wire in a tensioned configuration. The system also may incorporate a wire-tensioning device 28, namely, a wire-tensioning instrument termed a "tensioner," that applies tension to a surgical wire, such as tension to both opposing end regions of wire 24 at the same time. Tensioner 28 may be configured to apply tension with wire 24 wrapped around bone, and to maintain tension while the locking function of device 26 is being actuated. Further aspects of wire-locking devices that may be suitable for use in system 20 are described in the following patent documents, which are incorporated herein by reference: U.S. Pat. No. 5,810,825, issued Sep. 22, 1998; U.S. Pat. No. 6,017,347, issued Jan. 25, 2000; U.S. Pat. No. 6,120,505, issued Sep. 19, 2000; and U.S. Patent Application Publication No. 2010/0094294.

Cerclage assembly 22 may be connected to any suitable bone. For example, here, cerclage assembly 22, and particularly wire 24, encircle a sternum 30, which has been cut longitudinally, indicated at 32, to provide access to a chest cavity during open-heart surgery. In other embodiments, wire 24 may encircle only a portion the sternum's (or other bone's) circumference, by extending around only a portion of the sternum's perimeter and through the sternum. Further aspects of bones that may be suitable are described below in Section IV.

The tensioner may be equipped with a frame or body 34, a drive assembly 36 connected to the frame, and a carriage 38 operatively connected to the drive assembly. Carriage 38 also or alternatively may be termed a shuttle. Frame 34 may form a graspable handle portion or grip portion 40 to permit manual engagement and positioning of the tensioner, such as with one hand. Operation of the drive assembly may be performed by manual manipulation of a user control 42 thereof (e.g., a lever, knob, switch, button, etc.), which may result in transmission of power to the drive assembly, such as manual power or from a motor. For example, a surgeon may turn a crank 44 manually, such as with the surgeon's other hand. In any event, operation of the drive assembly may cause movement of carriage 38 parallel to an axis of travel 46 defined by the drive assembly. The axis of travel may (or may not) be at least substantially parallel to a longitudinal axis defined by tensioner 28 and/or frame 34.

FIG. 2 shows a fragmentary view of tensioner 28, wire 24, and locking device 26, in the absence of bone. Carriage 38 may be equipped with a securement assembly including at least one or a pair of fasteners 50 (i.e., anchor sites; also see FIG. 3) to permit attachment of opposing ends 52, 54 of wire 24 to the carriage. The "ends" or "end regions" of the wire, as used herein, represent respective wire regions disposed toward one or the other terminal of the wire with respect to an encircling or wrapped segment of the wire disposed in, on, and/or about bone. Anchor sites 50 may oppose one another in the securement assembly, such as opposingly flanking axis of travel 46. The anchor sites (fasteners 50) may be structured as hitching brackets 56 onto which the wire may be wrapped, to restrict slippage of the wire under tension. Alternatively, the anchor sites may be structured as clamps, among others. In any event, with wire 24 attached to the anchor sites and extending around bone, driven travel of the carriage away from a distal end 58 (which may be termed a nose) of the tensioner's frame 34 exerts a pulling force on both ends 52, 54 of the wire. The pulling force applies tension to the wire after slack in the wire is removed. As the wire is tensioned, the wire becomes cinched around bone, generally to apply radial compression to the bone.

A hitching bracket, which alternatively may be termed a cleat, a spool, or a winding site, generally includes any projecting structure about which a region of a wire can be wrapped to secure the wire region to the projecting structure in a configuration that resists slippage of the wire under tension. The projecting structure generally has a shape that permits the wire to be secured with a minimal amount of wrapping, to reduce the time spent wrapping and/or to permit use with a shorter wire and/or where the length of the wire is limiting.

Each hitching bracket may include one or at least a pair of projections 59 (e.g., wings/ears, a plate, or posts, etc.) around which the wire may be wrapped, such as in a figure-8 or figure-0 pattern, among others. In some embodiments, projections 59 may define respective planes that are at least substantially parallel to one another.

The hitching bracket is configured to resist slippage of the wire under tension. The hitching bracket may define at least one notch 60 to receive the wire. The notch (e.g., an end notch) may be tapered, such as at least generally V-shaped, with each wall of the notch being linear or curved in profile. For example, in the present illustration, each end notch 60 is formed by a linear wall at a base of projection 59 and a curved wall provided by a wall member 61 of carriage 38. Each notch may taper in a direction at least generally parallel to travel axis 46. In some embodiments, each hitching bracket 56 may include a pair of notches 60 arranged along a line that is at least generally parallel to travel axis 46. In some embodiments, each hitching bracket may include a pair of notches 60 that taper at least generally toward one another. Each notch 60 may form an opening into which a segment of wire 24 may be wedged, to restrict slippage of the wire. The notch may define a direction of taper, and the segment may be placed to extend transversely to the direction of taper.

Each hitching bracket may include a receiver region that at least generally defines a winding path for wrapping a wire around the hitching bracket. For example, the receiver region may be defined through at least one notch or through a pair of notches, among others. The receiver region may have a shape that resists slippage of the wire. The shape of the receiver region (and of the winding path for the wire) may be substantially rectangular and/or may have a length that is substantially greater than its width (e.g., at least about two-, five- or ten-fold greater). For example, the receiver region may be elongated in a direction at least substantially parallel to travel axis 46. In some embodiments, the width of the receiver region (e.g., the thickness of projection 59) may, for example, be about 1 to 5 millimeters or about 2 to 3 millimeters, among others. In any event, the hitching bracket may form a receiver region where the wire is doubled back sharply on itself at one or both opposing ends of the winding path (e.g., at one or two notches), when wrapped tightly onto the hitching bracket (such as when wrapped and tensioned), to form kinks in the wire that resist slippage on the hitching bracket.

The hitching bracket also may define a retainer slot 61a that receives the end region of the wire after the wire has been wrapped around the hitching bracket. Slot 61a may restrict the wire from unwrapping. The slot may be disposed at least generally between an opposing pair of end notches.

The use of hitching brackets may provide substantial advantages over other approaches to securing a wire to a tensioner. For example, a hitching bracket may be structured to have a fixed shape, with no parts that move relative to one another, and thus may be simple in design and use. Also, a hitching bracket may permit a wire to be quickly engaged with the hitching bracket by wrapping the wire around the hitching bracket, and to be removed easily when tensioning has been completed by unwrapping the wire. In some embodiments, the hitching bracket may be configured to secure a wire wrapped only about one time around the hitching bracket and/or less than about two times around the hitching bracket, which minimizes the length of wire needed for securement and minimizes the amount of wrapping required. Furthermore, a hitching bracket may provide a self-tightening configuration for the wire that causes the wire to be secured to the hitching bracket even more effectively as the wire is tensioned. For example, the wire may be wedged more tightly into notch 60 and/or kinked more sharply as tension is increased.

Tensioner 28 may include a guide portion 62 formed at distal end 58. The guide portion may receive a segment of each wire end and redirect the wire ends from opposed, divergent paths, which are transverse (e.g., at least substantially orthogonal) to axis of travel 46, to paths that extend in about the same direction, at least substantially parallel to the axis of travel. In other words, the guide portion may function to change the direction of forces exerted on the wire ends. In particular, substantially parallel forces exerted axially on the wire ends via the carriage and drive assembly may be converted to transverse forces exerted opposingly on the wire ends at positions closer to bone and/or closer to wire-locking device 26, to tension the wire around bone.

Guide portion 62 may include pulleys 64 to receive the wire ends (also see FIG. 3). The pulleys may be mounted pivotably to respective legs 66 that project distally from a body member 68 of frame 34. Legs 66 may be spaced from one another to form an opening 70 for receiving locking device 26 and, optionally, sections 72 of wire 24 projecting opposingly from ends of the locking device. Opening 70 also may permit a crimping or compression tool to access opposing sides of the locking device, to permit the wire to be locked to the locking device.

Carriage 38 may be pivotably connected to drive assembly 36 to balance or equalize the tension applied to opposing ends 52, 54 of wire 24. In particular, carriage 38 may be pivotable about a pivot axis 74 oriented transversely (e.g., at least substantially orthogonal) to axis of travel 46. (Pivotal motion of carriage 38 is indicated at 75 by pivot arrows adjacent each hitching bracket 56 and by a pivoted configuration of the carriage shown in phantom outline.) The ability of carriage 38 to pivot permits dynamic changes to a ratio of respective distances 76, 78 of hitching brackets 56 from distal end 58 of the tensioner. For example, if one of the wire ends is under less tension than the other, the carriage can pivot about pivot axis 74 to reposition the anchor site for one wire end farther from distal end 58 and the anchor site for the other wire end closer to the distal end, until tension is equalized (or further pivotal motion is blocked). Accordingly, the ability of the carriage to pivot may promote application of a more equalized tension to both ends of the wire, thereby reducing any tendency of the wire to be tightened asymmetrically around bone.

Tensioner 28 also may be equipped with a tension gauge 80. The gauge may be configured to permit a level of wire tension to be read from the gauge by visual inspection. Gauge 80 may include a tension indicator 82 (providing an index or pointer 84) and a series of reference marks or indicia 86 that represent different levels of tension applied to the wire. Tension indicator 82 may move along a channel 88 formed adjacent reference marks 86 or between separated parts of the series of reference marks (also see FIG. 3). The position of the tension indicator may correspond to the level of tension applied to the wire. Reference marks 86 may include graduations, alphanumeric characters, other symbols, a combination thereof, or the like. For example, in the present illustration, reference marks 86 include the letters "L," "M," and "H," to represent relative low, medium, and high levels of tension, respectively, on the wire. Thus, tension indicator 82 travels in a distal direction along channel 88 as tension is increased. In other examples, the reference marks may include numbers that correspond to a magnitude of force applied to the wire. In exemplary embodiments, intended only for illustration, the tension gauge may be configured to measure a force of about 20 to 60 pounds (i.e., about 90 to 270 Newtons), which corresponds to a tension on the wire of about 10 to 30 pounds (i.e., about 45 to 135 Newtons).

Tensioner 28 may have substantial 2-fold rotational symmetry about a central longitudinal axis defined by the tensioner. Accordingly, the tensioner may be turned over and used equivalently. For example, tension gauge 80 may be readable from opposing sides of the tensioner, namely, from the side facing toward the viewer in FIG. 2 and from an opposing side that is not visible in FIG. 2 (and that faces away from the viewer). To allow reading from opposing sides of the tensioner, pointer 84 and reference marks 86 may be duplicated on opposing sides of the tensioner. For example, tension indicator 82 may be visible from the opposing side of the tensioner and thus the opposing ends of the indicator may be structured equivalently to form pointers 84 on both ends of the indicator.

The ability to use the tensioner (e.g., to read tension levels) when pivoted 180 degrees facilitates operation of the tensioner in different orientations during a surgical tensioning procedure. For example, the tensioner may be pivoted about a transverse axis 89 defined generally by wire sections 72 extending opposingly from bone (and/or by bores of locking device 26 from which the wire sections extend). Thus, the tensioner may be pivoted about axis 89 to facilitate access to wire 24 and/or locking device 26 (e.g., locking studs thereof) from opposing sides of the locking device.

FIG. 3 shows an exploded view of tensioner 28. Drive assembly 36 may include a drive screw 90, which may be received in frame 34. The drive screw may include an external thread 91 disposed toward the leading end of the drive screw and a driver engagement structure, such as a hexagonal shaft 92 disposed at the trailing end of the drive screw. Rotation of the drive screw via a user control, such as crank 44, may drive translational motion of carriage 38. In some embodiments, the drive assembly may include a leadscrew assembly incorporating drive screw 90 and an internally threaded member or nut 94 that is threadably received on the drive screw. The nut may be restricted from turning with the drive screw, such that rotation of the drive screw causes relative translational motion of the nut with respect to the drive screw, in a direction parallel to the longitudinal axis of the drive screw. Alternatively, the drive screw may be part of a ball screw, among others.

Carriage 38 may be pivotably coupled to nut 94 for pivotal motion about pivot axis 74. For example, the carriage may be assembled around the nut, such as with axles 96 projecting from the nut and received in openings 98 of the carriage, or vice versa, or a combination thereof.

Carriage 38 (and nut 94) may be received in a cavity 100 defined by frame 34. Cavity 100 may extend transversely across the frame to permit anchor sites 50 to project from both opposing sides of the tensioner. One or both opposing walls of the cavity may engage carriage 38 to prevent the carriage from rotating with the drive screw.

FIG. 4 shows a sectional view of tensioner 28 with cerclage assembly 22 in phantom outline, before tensioning wire 24. When wire 24 is attached initially to carriage 38, the carriage may (or may not) be disposed toward the distal end of cavity 100.

Drive screw 90 may be disposed in a bore 106 defined by frame 34 and may have a biased position in bore 106 (and with respect to frame 34), along travel axis 46. For example, the drive screw may be urged away from distal end 58 of the tensioner by a biasing element, such as an elastic device (e.g., a spring, such as a coil spring 108, leaf spring, etc.). Here, spring 108 engages a flange 110 formed on the drive screw and a shoulder 112 defined by frame 34 in bore 106, to urge the drive screw axially toward a proximal end 114 of the tensioner. In this configuration, tension indicator 82 is disposed toward the proximal end of channel 88, reflecting a low level of tension (or no tension) on wire 24 (also see tension gauge 80 of FIG. 2).

FIG. 5 shows another sectional view of tensioner 28, taken as in FIG. 4, but after tensioning the wire with the tensioner. To produce the configuration of FIG. 5, crank 44 has been rotated, indicated at 116, to produce net longitudinal travel, indicated at 118, of carriage 38 (and nut 94) with respect to frame 34 and drive screw 90. However, the net travel with respect to the frame may be less than with respect to the drive screw. In particular, as wire 24 is tensioned, the wire exerts an opposing force on carriage 38, towards distal end 58, which urges drive screw 90 from its biased position. When sufficient tension is applied to wire 24, and thus a sufficient opposing force applied to the carriage, nut, and drive screw, spring 108 may become compressed, indicated at 120, which results in drive screw 90 moving axially with respect to frame 34, indicated at 122, toward distal end 58. In other embodiments, a biasing element (such as spring 108) may be configured to be stretched/distracted as tension increases.

Tension indicator 82 may be connected to and disposed adjacent a distal end of drive screw 90. The tension indicator may be connected pivotably, to permit the tension indicator to remain oriented in the same direction in channel 88 while the drive screw rotates. In any event, drive screw 90 and tension indicator 82 may be coupled positionally along the travel axis, such that a change in axial position of the drive screw in response to increased tension produces a corresponding change in position of the tension indicator with respect to reference marks 86 (see FIG. 2). Thus, tension indicator 82 also travels toward distal end 58 with increased tension, reflecting a change in tension measurable by the tension gauge.

Spring 108 (or another biasing element) may have any suitable properties. By selection of a spring with a suitable spring constant, the force necessary to produce spring compression (or distraction) is in the same range as a desired force to be applied to the wire to achieve proper tensioning of the wire. Also, by using a spring with a suitable spring constant, compression (or distraction) of the spring and associated axial travel of the drive screw by a predefined distance reflects a predefined amount of tension on the wire. The spring also may act as a buffer or safety mechanism that absorbs some of the force applied to drive screw 90 via crank 44, to provide better control of and a more gradual increase in, tension applied to the wire as the crank is turned.

Tensioner 28 may be capable of maintaining wire 24 under tension without continued manual engagement of crank 44, due to friction between drive screw 90 and nut 94. Accordingly, a surgeon may, for example, hold the tensioner with only one hand, after placing the wire under tension, while using the other hand to lock the cerclage assembly in place around bone.

II. Wires

The system disclosed herein may include at least one wire. The terms "wire" and "cable" in surgical and/or orthopedic applications are often used to distinguish respective single-stranded (i.e., monofilament and/or monolithic) and multi-stranded (i.e., multi-filament) structures. Wires and cables thus may have distinct uses and properties (e.g., distinct flexibilities and tendencies to kink and fray). However, the term "wire," as used herein, is intended to encompass single-stranded and multi-stranded structures.

A surgical wire may have any suitable composition, shape, size, and condition. The wire is typically formed of metal, particularly a biocompatible metal, such as stainless steel. The wire may (or may not) be generally round in cross section (e.g., circular, oval, etc.). The wire is elongate, with a length that is generally substantially greater than the circumference of a target site of bone to be encircled. The wire may have any suitable diameter, such as a diameter of about 0.4 to 2 millimeters, 0.5 to 1.5 millimeters, or about 0.8 to 1 millimeter, among others. The wire may be supplied in a sterilized condition (e.g., autoclaved, gamma-irradiated, treated with a gas (such as ethylene oxide), etc.).

III. Locking Devices

The system disclosed herein may include at least one locking device that is implanted with a wire to secure the wire to bone. The locking device may engage the wire at a pair of sites along the wire to hold the sites in position with respect to one another. The locking device may be structured as a clip, a block, a plate, a pair of attached sleeves, or a combination thereof, among others. In any event, the locking device may define one, two, or more apertures for receiving one or more segments of a wire. In some embodiments, the shape of the aperture may be modified after a segment of wire has been received, such as to crimp the wire, to lock the segment of wire to the locking device. Further aspects of locking devices that may be suitable are described in the following patent documents, which are incorporated herein by reference: U.S. Pat. No. 5,810,825, issued Sep. 22, 1998; U.S. Pat. No. 6,017,347, issued Jan. 25, 2000; U.S. Pat. No. 6,120,505, issued Sep. 19, 2000; and U.S. Patent Application Publication No. 2010/0094294.

IV. Methods Of Wire Tensioning And/Or Bone Fixation

The system disclosed herein provides methods of tensioning a surgical wire, fixing a bone with a tensioned wire, and/or installing a surgical wire with a tensioning device. The method steps presented below in this Section and elsewhere in the present disclosure may be performed in any suitable combination and in any suitable order.

A bone may be selected to receive a surgical wire and/or cerclage assembly. The bone may be any suitable bone of a human or other vertebrate species. Exemplary bones that may be suitable include at least one bone of the arms (humerus, radius, and/or ulna), wrists (carpal), hands (metacarpal and/or phalange), legs (femur, tibia, and/or fibula), feet (talus, calcaneus, tarsal, metatarsal, and/or phalange), ribs, spine, pelvis, or cranium, or a sternum, clavicle, mandible, or scapula, among others. The bone selected may have a discontinuity (e.g., a fracture, a cut, a nonunion, or the like), may be otherwise structurally compromised (e.g., osteoporotic bone), or may be connected to injured soft tissue (e.g., an injured ligament and/or tendon).

A wire may be wrapped around the bone or wrapped around a portion thereof (e.g., by placing the wire through the bone and bringing the ends of the wire around the bone to cross each other in a parallel arrangement, with the ends extending in opposite directions). The wire also may be assembled with a locking device, such as by placing one or more sections of the wire into one or more receivers of the locking device. Assembly with the locking device may be performed before, during, and/or after the wire has been wrapped around the bone or bone portion.

The wire may be connected to a tensioner. Generally, connection of the wire to a tensioner may be performed after wrapping the wire around bone and assembling the wire with a locking device (e.g., see FIGS. 1 and 2). In any event, each end of the wire may be secured to a carriage of the tensioner. Securement may be performed using any suitable fastener structure of the carriage. In some examples, the fastener structure may actively engage a wire by moving a portion of the fastener structure into opposing engagement of the wire. For example, the fastener structure may be at least one clamp that can be actuated to secure the wire ends. In other examples, the fastener may be a hitching bracket that engages the wire as the wire is wrapped around the hitching bracket, such as wrapped at least once and/or wrapped less than about twice around the hitching bracket. The wire may be kinked one or more times (e.g., at least twice) at each hitching bracket as a result of wrapping the wire around the hitching bracket and/or tensioning the wire on the hitching bracket. A segment of the wire may be disposed in a notch, such as a tapered notch, provided by each hitching bracket. The notch may define a direction in which the notch tapers and the segment of wire may be disposed in the notch with the segment extending transversely, such as at least substantially orthogonally, to the direction in which the notch tapers. In some cases, each end region of the wire may be disposed in a pair of notches, such as tapered notches, provided by each hitching bracket. The tapered notches may taper toward each other.

The respective ends of the wire may be bent by about 90 degrees as they extend from the bone and/or locking device to their attachment sites on the carriage. In particular, the tensioner may form a guide path that directs the wire ends from an opposingly parallel configuration (with segments of the wire ends extending in opposite parallel directions adjacent bone), to another parallel configuration (with more terminal segments of the wire ends extending in the about same direction from the distal end of the tensioner to the carriage. The wire may bend along the guide path through contact with a guide structure, such as at least one pulley that contacts each wire end.

Power may be supplied to the tensioner to drive the carriage parallel to an axis of travel defined by a drive assembly of the tensioner. The carriage may be driven in a direction generally away from the bone. The power may be supplied manually, such as by turning at least a portion of the drive assembly by hand, or via a motor. Movement of the carriage may tension the wire via its ends. The tension applied to each wire end may be balanced dynamically by pivotal motion of the carriage about a transverse axis, to adjust the angular position of the carriage, as the carriage is driven along the axis of travel.

Supplying power to the tensioner may be stopped when a suitable level of tension has been achieved. The level of tension may be measured during and/or after supplying power by observing at least one tension gauge of the tensioner. Alternatively, the tensioner may lack a tension gauge, and a suitable level of tension may be achieved using another tension indicator (e.g., by feel, visual inspection of the wire and/or bone, etc.).

The wire may be secured around the bone. The wire may be secured in placed around the bone while the tensioner maintains the wire under tension. The wire may be secured or locked by actuating a locking device assembled with the wire (or twisting the wire ends together). For example, the locking device may be deformed with a crimping tool, such as pliers, to lock the wire to the locking device. In exemplary embodiments, the locking device may be actuated by applying pressure to one or more locking studs of the locking device.

Excess wire may be removed. For example, the wire may be cut near the locking device or where the wire is twisted together, to separate the wire ends from a segment of the wire encircling bone.

V. Kits

The system disclosed herein provides kits for tensioning a surgical wire and/or fixing a bone with a tensioned wire. The kits may comprise any combination of at least one surgical wire, at least one locking device, a tensioner, one or more clamps to grip and manipulate the wire, at least one wire cutter, at least one compression tool (e.g., a crimping tool) to actuate the locking device, or the like. The components of a kit may be supplied in a sterile package. Some of the components may be configured to be re-used (e.g., the tensioner, clamps, wire cutter, and compression tool) and others may be configured to be used only once (e.g., the wire and the locking device).

VI. EXAMPLES

The following examples describe selected aspects and embodiments of the present disclosure, including another exemplary tensioner for use with surgical wire. These examples are intended for illustration and should not limit the entire scope of the present disclosure.

Example 1

Tensioner with Dual Tension Gauges

Figure 7:
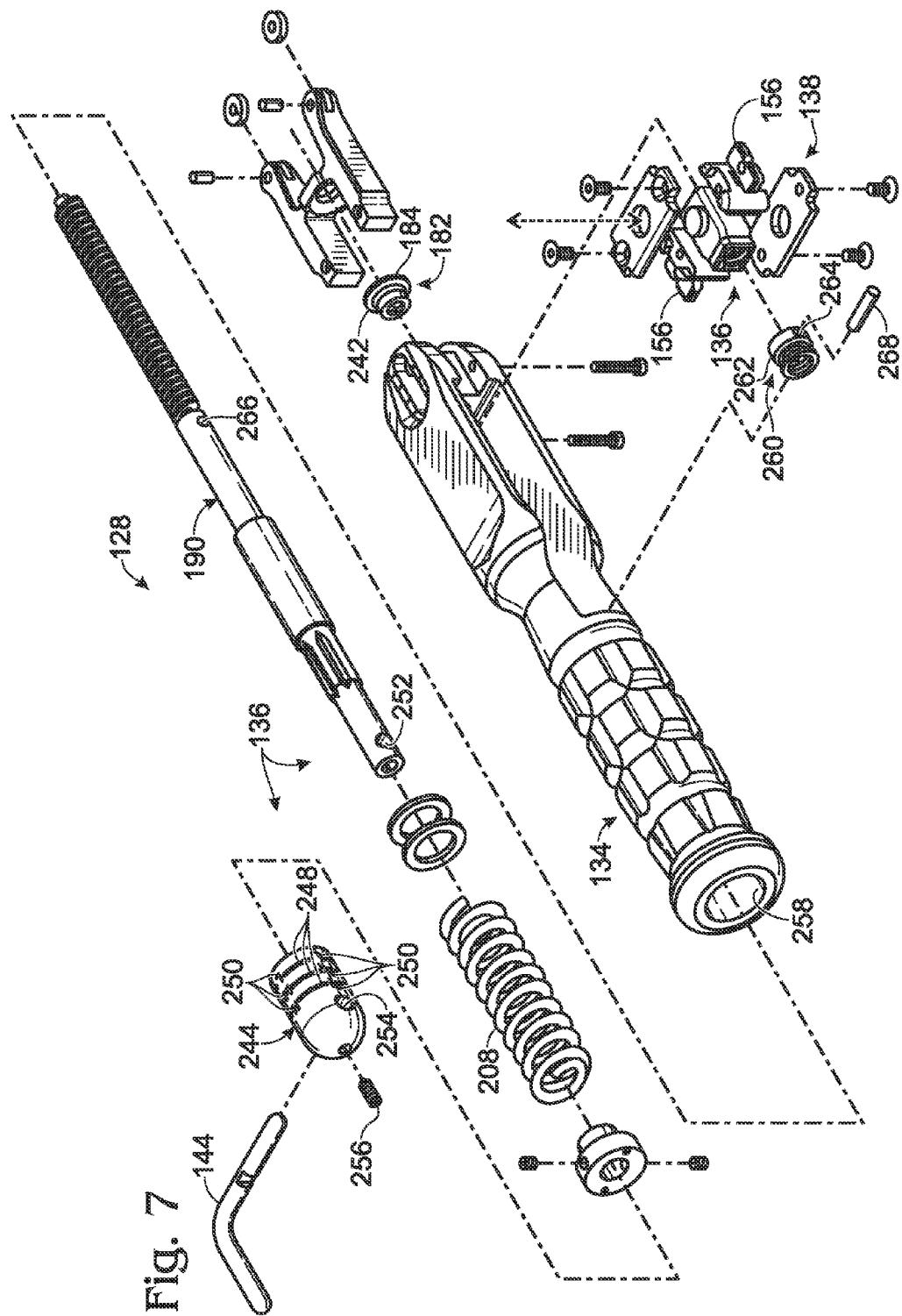
FIG. 7 is an exploded view of the tensioner of FIG. 6, with tensioner components arranged similarly to the exploded view of FIG. 3.

This example describes an exemplary tensioner 128 equipped with a pair of axially spaced, distal and proximal tension gauges 180, 230; see FIGS. 6 and 7.

Tensioner 128 of FIGS. 6 and 7 is structurally and functionally similar to tensioner 28 (see FIGS. 1 to 5). Accordingly, to highlight the similarities between the two tensioner embodiments, components of tensioner 128 that are analogous or similar to those of tensioner 28 are identified with reference numbers corresponding to those of tensioner 28, except incremented by 100. For example, tensioner 128 includes a frame 134, a drive assembly 136 including a crank 144 and a drive screw 190, and a carriage 138 supporting hitching brackets 156. Components or features that are absent from tensioner 28, or warrant special mention, are labeled with numeric identifiers starting at 230.

Tension gauges 180 and 230 are spaced from one another axially, that is, along a long axis 232 defined by tensioner 128. Gauge 180 and gauge 230 are formed near opposing ends of the tensioner, with distal gauge 180 and proximal gauge 230 disposed, respectively, near a distal end 158 and a proximal end 214 of the tensioner.

Each gauge may be configured to be readable from opposing sides or faces of tensioner 128. For example, each of the gauges may be readable from opposing directions orthogonal to the long axis of the tensioner and/or orthogonal to a plane defined by the laterally spaced, longitudinal paths of the wire.

The incorporation of gauges near each end of the tensioner may be advantageous to a surgeon for at least several reasons. First, the presence of two gauges accommodates different tensioning styles and preferences. Second, the visibility of each gauge may vary during a tensioning procedure and/or among procedures. Third, the surgeon can shift attention from a position near bone to a position between the surgeon's arms and still obtain the same tension reading.

Each tension gauge may include a tension indicator 182, 234 providing a pointer or index 184, 236. The pointer or index can be compared with a series of reference marks 186, 238 to read the amount of tension.

Distal gauge 180 operates substantially as described above for gauge 80, with a few minor changes. The arrangement of reference marks is altered slightly, with the "M" omitted and only three levels of tension marked with line segments 240. Also, tension indicator 182 is secured to a leading end of drive screw 190 such that indicator 182 rotates with the drive screw (see FIG. 7). Indicator 182 defines a circumferential groove 242 that provides pointer 184 at any permitted rotational position of drive screw 190.

Proximal gauge 230 is conceptually similar to distal gauge 180 but has a number of distinctions. Both gauges measure wire tension based on the axial position of at least a part of drive assembly 136 relative to frame 134. As wire tension increases, spring 208 is compressed and drive screw 190 shifts in axial position toward the distal end of the tensioner (e.g., see FIGS. 4 and 5 and corresponding text for tensioner 28). A portion of each gauge 180, 230 shifts in axial position with the drive screw. Gauge 180 relies on axial movement of tension indicator 182 (with drive screw 190) relative to reference marks 186 provided by frame 134. In contrast, gauge 230 relies on axial movement of reference marks 238 (with drive screw 190) relative to tension indicator 234 provided by frame 134. In other embodiments, the proximal gauge, like the distal gauge, may be formed by a series of reference marks provided by the frame and a tension indicator provided by the drive assembly.

The components of gauge 230 are formed near the proximal end of the tensioner. Reference marks 238 are provided by a head or end cap 244 of drive assembly 136. Pointer 236 is provided by an end surface 246 of frame 134.

Head 244 carries a series of graduations 248 and alphanumeric marks 250 (namely, the letters "L," "M," and "H") on lateral surfaces of the head. The series of graduations and letters are duplicated at multiple positions around the head (in this case four) to permit the graduations and letters to be visible at all rotational positions of the head produced by turning crank 144. The graduations of proximal gauge 230 may have the same spacing as graduations of distal gauge 180. The gauges also may share two or more of the same alphanumeric marks, but ordered in opposing directions. For example, gauge 180 has "L" and "H" arranged proximally to distally, while gauge 230 has "L" (and "M") and "H" arranged distally to proximally.

Head 244 is fixed and locked to drive screw 190 with crank 144 (see FIG. 7). The head is received on the trailing end of screw 190 to align apertures 252, 254. Crank is received in the aligned apertures such that the head and the drive screw turn together. The crank is held in place with a lock screw 256. Head 244 is received in a bore 258 formed at the proximal end of frame 134 and sized to permit the head to slide axially (in response to changes in tension).

Drive screw 190 has an axial travel limit in a proximal direction determined by a travel stop 260 (see FIG. 7). Here, stop 260 is a collar 262. The drive screw is placed through collar 262 to align apertures 264, 266 of the collar and drive screw. A locking member 268 is inserted into the aligned apertures to lock the collar in place. The collar may be used to pre-compress spring 208.

Example 2

Selected Embodiments

This example describes selected embodiments of the present disclosure, presented as a series of indexed paragraphs. These embodiments are intended for illustration and should not limit the entire scope of the present disclosure.

1. A device for tensioning a surgical wire, comprising: (A) a frame including a distal end portion; (B) a drive assembly connected to the frame and defining an axis of travel; (C) a carriage including opposing anchor sites configured to provide attachment of opposing end regions of a surgical wire extending to the anchor sites from the distal end portion of the frame, the carriage being connected to the drive assembly such that power supplied to the drive assembly drives the carriage away from the distal end portion of the frame, thereby providing an ability to apply tension to both end regions of the wire; and (D) first and second tension gauges formed at spaced positions along the device.

2. The device of paragraph 1, wherein the tension gauges are formed near opposing ends of the device.

3. The device of paragraph 1 or paragraph 2, wherein each of the first and second tension gauges includes a series of reference marks corresponding to different amounts of tension, wherein the first tension gauge has reference marks provided by the frame and the second tension gauge has reference marks provided by the drive assembly and configured to rotate relative to the frame.

4. The device of any one of paragraphs 1 to 3, wherein axial displacement of at least a portion of the drive assembly relative to the frame changes an amount of tension measured by each of the first and second tension gauges.

5. The device of paragraph 4, wherein the drive assembly includes a drive screw in threaded engagement with the carriage, and wherein axial displacement of the drive screw with respect to the frame changes the amount of tension measured by each of the first and second tension gauges.

6. The device of any one of paragraphs 1 to 5, wherein the device defines a long axis, and wherein each of the first and second tension gauges is readable from opposing directions orthogonal to the long axis.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

The invention claimed is:

1. A method of bone fixation, comprising:
    disposing a surgical wire around bone;
    attaching opposing end regions of the wire to a carriage;
    applying tension to both end regions of the wire by turning a screw having a longitudinal axis defining a first axis, to drive movement of the carriage away from the bone along the first axis, the tension being dynamically balanced between the end regions, as the screw is being turned, by pivotal motion of the carriage about a second axis that is transverse to the first axis; and
    securing the wire around the bone.

2. The method of claim 1, where the carriage includes a pair of hitching brackets, and wherein the step of attaching includes a step of wrapping each end region of the wire around a hitching bracket.

3. The method of claim 2, wherein the step of wrapping disposes a portion of each end region of the wire in a notch of a hitching bracket, and wherein the step of applying tension wedges the portion of the wire into the notch.

4. The method of claim 1, wherein the step of securing includes a step of actuating a locking device that is assembled with the wire.

5. The method of claim 1, wherein the carriage and the screw are included in a tensioning device comprising a tension gauge, further comprising a step of reading from the tension gauge an amount of tension applied to the wire.

6. The method of claim 5, wherein the tension gauge is readable from opposite sides of the tensioning device.

7. The method of claim 5, wherein the tension gauge is a first tension gauge, wherein the tensioning device includes a second tension gauge to measure a tension of the wire, and wherein the second tension gauge is spaced from the first tension gauge along a line parallel to the first axis.

8. The method of claim 7, wherein axial displacement of the screw relative to a frame of the tensioning device changes an amount of tension readable from each of the first and second tension gauges.

9. The method of claim 8, wherein each of the first and second tension gauges includes a series of reference marks corresponding to different amounts of tension on the wire, wherein the first tension gauge has a series of reference marks provided by the frame, and wherein the second tension gauge has a series of reference marks provided by a drive assembly including the screw and configured to be turned relative to the frame.

10. The method of claim 1, wherein the carriage is connected to a frame, and wherein the screw is configured to move axially with respect to the frame in response to changes in tension applied to the wire.

11. The method of claim 10, wherein the screw includes or is attached to a tension indicator that moves axially with the screw, and wherein the frame includes a series of reference marks arranged to form at least part of a tension gauge with the tension indicator.

12. The method of claim 1, wherein the screw is turned with a hand-operated crank.

13. The method of claim 1, wherein the opposing end regions of the wire are attached individually to a pair of distinct anchor sites of the carriage.

14. A method of bone fixation, comprising:
    disposing a surgical wire around bone;
    wrapping opposing end regions of the wire at least once around respective hitching brackets of a carriage;
    applying tension to both end regions of the wire by driving movement of the carriage away from the bone; and
    securing the wire around the bone,
    wherein the step of wrapping includes a step of placing a portion of each end region of the wire in a tapered notch defined by one of the hitching brackets, with the portion extending transversely to a direction of taper of the notch, and wherein the step of applying tension wedges the portion into the tapered notch.

15. The method of claim 14, wherein the step of wrapping includes a step of kinking each opposing end region of the wire.

16. The method of claim 14, wherein the step of wrapping includes a step of wrapping each end region of the wire less than two times around a hitching bracket.

17. The method of claim 14, wherein the hitching brackets include a pair of retainer slots, and wherein the step of wrapping includes a step of disposing each end region of the wire in a retainer slot to restrict unwrapping of the end region from a hitching bracket.

18. A method of bone fixation, comprising:
disposing a surgical wire around bone;
attaching opposing end regions of the wire to a carriage;
applying tension to both end regions of the wire by turning a screw having a longitudinal axis defining a first axis, to drive movement of the carriage away from the bone along the first axis, the tension being dynamically balanced between the end regions by pivotal motion of the carriage about a second axis that is transverse to the first axis; and
securing the wire around the bone,
wherein the carriage includes a pair of hitching brackets, and wherein the step of attaching includes a step of wrapping each end region of the wire around a hitching bracket.

19. A method of bone fixation, comprising:
disposing a surgical wire around bone;
attaching opposing end regions of the wire to a carriage;
applying tension to both end regions of the wire by turning a screw having a longitudinal axis defining a first axis, to drive movement of the carriage away from the bone along the first axis, the tension being dynamically balanced between the end regions by pivotal motion of the carriage about a second axis that is transverse to the first axis; and
securing the wire around the bone,
wherein the carriage and the screw are included in a tensioning device comprising a tension gauge, further comprising a step of reading from the tension gauge an amount of tension applied to the wire.

* * * * *